(12) United States Patent
Singh et al.

(10) Patent No.: US 9,272,995 B2
(45) Date of Patent: Mar. 1, 2016

(54) PROCESS FOR PRODUCING IONIC LIQUIDS

(71) Applicants: Rajendra P. Singh, Broomfield, CO (US); Jerry Lynn Martin, Superior, CO (US); Joseph Carl Poshusta, Broomfield, CO (US)

(72) Inventors: Rajendra P. Singh, Broomfield, CO (US); Jerry Lynn Martin, Superior, CO (US); Joseph Carl Poshusta, Broomfield, CO (US)

(73) Assignee: CoorsTek Fluorochemicals, Inc., Arvada, CO (US)

( * ) Notice: Subject to any disclaimer, the term of this patent is extended or adjusted under 35 U.S.C. 154(b) by 0 days.

(21) Appl. No.: 13/770,774

(22) Filed: Feb. 19, 2013

(65) Prior Publication Data

US 2014/0235873 A1 Aug. 21, 2014

(51) Int. Cl.
*C07D 217/08* (2006.01)
*C07D 207/04* (2006.01)

(52) U.S. Cl.
CPC .................................... *C07D 207/04* (2013.01)

(58) Field of Classification Search
None
See application file for complete search history.

(56) References Cited

PUBLICATIONS

Heckel et al. Tetrahedron: Asymmetry (2013), 24(18), 1127-1133.*
Lethesh et al. Journal of Physical Chemistry B (2011), 115(26), 8424-8438.*
Zhou et al. Chemistry—A European Journal (2006), 12(8), 2196-2212.*
Yim et al. Bull. Korean Chem. Society (2007), vol. 28(9) 1567-1572.*
Odinets et al Dalton Transactions (2010) 39(17), 4170-4178.*
Zou et al. Chinese Journal of Chemistry (2009) 27(8), 1492-1500.*

* cited by examiner

*Primary Examiner* — Nyeemah A Grazier
(74) *Attorney, Agent, or Firm* — Don D. Cha; Hamilton DeSanctis & Cha, LLP.

(57) ABSTRACT

The present invention provides a method for producing ionic liquids without the use of a volatile solvent and/or water. In some embodiments, methods of the invention allow a continuous process for producing ionic liquids.

26 Claims, 1 Drawing Sheet

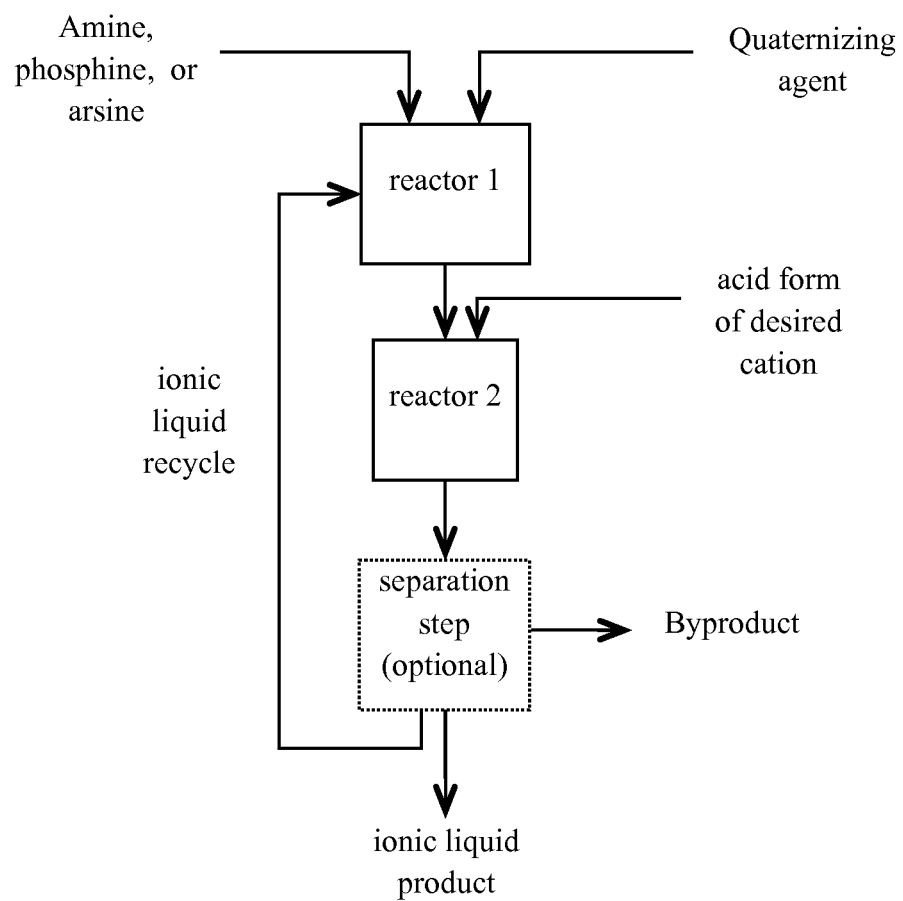

PROCESS FOR PRODUCING IONIC LIQUIDS

FIELD OF THE INVENTION

The present invention relates to a method for producing ionic liquids without the use of a volatile solvent and/or water. In some embodiments, methods of the invention can be used in a continuous process.

BACKGROUND OF THE INVENTION

Typical ionic liquids are non-volatile and non-flammable. In addition, they have wide electrochemical stability window and high ionic conductivity. These properties make ionic liquids (e.g., salts with melting points below 100° C.) useful for a wide variety of applications, including as electrolytes in batteries, capacitors and solar cells. For electrochemical applications, very high purity ionic liquids are required.

Conventional methods for manufacturing ionic liquids use batch processes and utilize organic solvents that must eventually be removed in order to use ionic liquids as electrolytes. Typical methods for producing ionic liquids involve a quaternization step to produce the required cation, followed by a metathesis step to substitute the required anion. In many cases, the salt produced by the quaternization step is solid at room temperature, which complicates handling and makes it difficult to utilize a continuous process.

Because a continuous process would greatly increase the efficiency of producing ionic liquids, there is an intense interest in developing a continuous ionic liquid producing process. Moreover, if one can eliminate the use of a solvent in ionic liquid producing process, it would further enhance ionic liquid producing process and greatly reduce the overall time and cost by eliminating a need to separate and/or dispose the solvent.

SUMMARY OF THE INVENTION

Some aspects of the invention provide a process for producing ionic liquids without the use of a volatile solvent. Such a process typically comprises:

reacting a compound of the formula Q with a quaternizing agent of the formula $R^1X$ in the absence of a volatile solvent under conditions sufficient to produce a quaternary salt of the formula:

$[R^1Q]^+X^-$ reacting said quaternary salt with an acidic form of an ionic liquid counter anion compound of the formula $HR_F$ under conditions sufficient to produce said ionic liquid of the formula $[R^1Q]^+R_F^-$ and a volatile acid of the formula HX, wherein
Q is an amine, phosphine, or arsine;
$R^1$ is a quaternizing moiety, such that $[R^1Q]^+$ forms an ionic liquid cation;
X is a leaving group;
$R_F$ is an ionic liquid anion moiety.

In some embodiments, Q is an amine heterocycle moiety having three to six carbon atoms in the ring system. Within these embodiments, in some instances Q is selected from the group consisting of pyrrolidine, imidazole, pyridine, and piperidine, each of which is optionally substituted.

Yet in other embodiments, no solid is produced during said process of producing said ionic liquid.

Still in other embodiments, the reaction temperature of said step of reacting said compound of formula Q with said quaternizing agent of the formula $R^1X$ is in the range from about 50° C. to about 200° C.

In other embodiments, the process further comprises the step of separating said volatile acid from said ionic liquid.

Yet still in other embodiments, said process is a continuous process.

In one particular embodiments, said ionic liquid anion moiety is of the formula $[YSO_2]_2N^-$, wherein each Y is independently F or a fluorohydrocarbon. In some instances, each Y is independently F or perfluorohydrocarbon. Yet in other instances, each Y is independently F or trifluoromethyl. In one particular instance, ionic liquid anion is bis(trifluoromethylsulfonyl)-imide or bis(fluorosulfonyl)imide.

Still yet in other embodiments, said step of reacting said compound of formula Q with said quaternizing agent of the formula $R^1X$ is conducted in a nonvolatile solvent. In some instances, said nonvolatile solvent is an ionic liquid solvent. In some cases, the ionic liquid solvent is of the formula $[R^1Q]^+R_F^-$, wherein $R^1$, Q and $R_F$ are those defined herein.

Another aspect of the invention provides a process for producing an ionic liquid of the formula $[R^1Q^1]^+R^1_F^-$. Such a process generally includes:

reacting a nitrogen atom containing heterocycle compound of the formula $Q^1$ with a quaternizing agent of the formula $R^1X$ in the absence of a volatile solvent under conditions sufficient to produce a quaternary salt of the formula:

$[R^1Q^1]^+X^-$ reacting said quaternary salt with a fluorinated acidic form of an ionic liquid counter anion compound of the formula $HR^1_F$ under conditions sufficient to produce said ionic liquid of the formula $[R^1Q^1]^+R^1_F^-$ and a volatile acid of the formula HX, wherein
$Q^1$ is a nitrogen atom containing heterocycle;
$R^1$ is a quaternizing moiety, such that $[R^1Q^1]^+$ forms a nitrogen-atom containing heterocycle ionic liquid cation;
X is a leaving group;
$R^1_F$ is a fluorinated ionic liquid anion moiety.

In some embodiments, said nitrogen-atom containing heterocycle compound comprises three to six carbon atoms in the ring system. In some instances, said nitrogen-atom containing heterocycle compound is selected from the group consisting of pyrrolidine, imidazole, pyridine, and piperidine, each of which is optionally substituted.

Yet in other embodiments, said ionic liquid anion moiety is of the formula $[YSO_2]_2N^-$, wherein each Y is independently F or a fluorohydrocarbon. In some instances, each Y is independently F or perfluorohydrocarbon. Yet in other instances, each Y is independently F or trifluoromethyl. In one particular embodiments, said ionic liquid anion is bis(trifluoromethylsulfonyl)imide or bis(fluorosulfonyl)imide.

Yet another aspect of the invention provides an ionic liquid having no more than 100 parts per million by weight of water, no more than 100 parts per million by weight of halide and/or less than 100 parts per million by weight solvent.

Still another aspect of the invention provides a process for producing a salt of the formula $[R^1Q^1]^+R^1_F^-$. Such a process typically includes:

reacting a nitrogen atom containing heterocycle compound of the formula $Q^1$ with a quaternizing agent of the formula R¹X in the absence of a volatile solvent under conditions sufficient to produce a quaternary salt of the formula:

reacting said quaternary salt with a fluorinated acid of the formula $HR^1_F$ under conditions sufficient to produce said salt of the formula $[R^1Q]^+R^1_F{}^-$ and a volatile acid of the formula HX, wherein
- $Q^1$ is a nitrogen atom containing heterocycle;
- $R^1$ is a quaternizing moiety, such that $[R^1Q^1]^+$ forms a nitrogen-atom containing heterocycle cation;
- X is a leaving group; and
- $R^1_F{}^-$ is a fluorinated anion.

In some embodiments, said fluorinated anion is of the formula $[YSO_2]_2N^-$, where each Y is independently F or a perfluorinated hydrocarbon group.

Yet in other embodiments, said process is a continuous process.

Still another aspect of the invention provides a process for producing an ionic liquid of the formula $[R^1Q^1]^+R^1_F{}^-$. In this aspect of the invention, said process comprises:

reacting a nitrogen atom containing heterocycle compound of the formula $Q^1$ with a quaternizing agent of the formula $R^1X$ in the presence of an ionic liquid solvent under conditions sufficient to produce a quaternary salt of the formula:

reacting said quaternary salt with a fluorinated acidic form of an ionic liquid counter anion compound of the formula $HR^1_F$ in the presence of said ionic liquid solvent under conditions sufficient to produce said ionic liquid of the formula $[R^1Q]^+R^1_F{}^-$ and a volatile acid of the formula HX, wherein
- $Q^1$ is a nitrogen atom containing heterocycle;
- $R^1$ is a quaternizing moiety, such that $[R^1Q^1]^+$ forms a nitrogen-atom containing heterocycle ionic liquid cation;
- X is a leaving group;
- $R^1_F$ is a fluorinated ionic liquid anion moiety, and wherein said ionic liquid solvent is said ionic liquid of the formula $[R^1Q^1]^+R^1_F{}^-$.

In some embodiments, at least a portion of the ionic liquid solvent is recycled. As used herein, unless the context requires otherwise, the term "recycled" refers to recovering and reusing the ionic liquid solvent in the same process.

Still in other embodiments, at least a portion of said ionic liquid that is produced is used as the ionic liquid solvent in said process. Thus, since the ionic liquid that is produced in the process is same as the ionic liquid solvent that is used in the reaction, some embodiments of the invention utilize at least a portion of the product that is produced as the solvent.

The volatile acid (HX) that is produced in the reaction can be removed by any of the separation methods known to one skilled in the art. In one embodiment, the volatile acid is removed by contacting said ionic liquid with an inert gas stream. In such embodiment, one can bubble an inert gas stream into the ionic liquid or simply provide a stream of inert gas on or near the surface of the ionic liquid to remove the volatile acid.

Alternatively, the volatile acid can be removed by subjecting the ionic liquid to a reduced pressure. As used herein, the term "reduced pressure" refers to a pressure less than ambient pressure, typically 100 mm of Hg or less, often 50 mm of Hg or less, often 10 mm of Hg or less, and most often 1 mm of Hg or less. In general, reduced pressure condition is achieved using a vacuum pump or some other similar means.

It should be appreciated that since ionic liquids are salts, they have a significantly less vapor pressure compared to the volatile acid. Accordingly, subjecting the product to an inert gas stream or a reduced pressure results in less than 5% loss by weight of ionic liquid, typically less than 1% loss by weight, and often less than 0.5% loss by weight.

Some aspects of the invention provide a continuous process for producing high-purity ionic liquids. In some embodiments, methods of the invention avoid producing solid intermediates. Still in other embodiments, methods of the invention result in superior purity of ionic liquids and/or a lower overall cost than conventional methods. One of the major differences and advantages of the invention is that methods of the invention do not require the use of volatile solvents.

BRIEF DESCRIPTION OF THE DRAWINGS

FIG. 1 a schematic illustration of one particular embodiment of the invention for producing ionic liquids in a continuous process.

DETAILED DESCRIPTION OF THE INVENTION

Some aspects of the invention provide a process for producing ionic liquids without the use of a volatile solvent. As used herein, the term "volatile solvent" refers to a liquid compound having a pure component vapor pressure of 1 mm Hg or more, typically 20 mm Hg or more, and often 100 mm Hg or more at standard temperature, i.e., 20° C. Thus, typical solvents that are used in conventional methods, such as dimethylformide (DFM), dimethylsulfoxide (DMSO), tetrahydrofuran (THF), methylene chloride, chloroform, carbon tetrachloride, ethyl ether, acetonitrile and methanol are all examples of volatile solvents. Other examples of volatile solvents include, but are not limited to, water, perfluorinated hydrocarbons and supercritical carbon dioxide are also volatile solvents.

One particular aspect of the invention provides a process for producing an ionic liquid of the formula $[R^1Q]^+R_F{}^-$, where Q is an amine, phosphine, or arsine moiety; $R^1$ is a quaternizing moiety, such that $[R^1Q]^+$ forms an ionic liquid cation moiety; and $R_F$ is an ionic liquid anion moiety. Typically Q is a tertiary amine, phosphine or arsine moiety such that when $R^1$ is attached to Q, the resulting $R^1Q^+$ forms the cationic portion of an ionic liquid. The term "tertiary amine" and the corresponding phosphine and arsine refer to an amino, phosphino and arsino compound of the formula $R^aR^bR^cM$, where M is N, P or As, respectively, and each of $R^a$, $R^b$ and $R^c$ is independently an acylic or cyclic hydrocarbon that is optionally substituted. Or two or more $R^a$, $R^b$ and $R^c$ together with M form a cyclic amino, phosphino or arsino compound. It should also be noted that when $R^a$ and $R^b$ together with M form an unsaturated cyclic ring system such as an aromatic amino, phosphino or arsino compound, $R^c$ is absent. Similarly, if $R^a$ forms a double bond with M in an acylic compound, $R^c$ is absent. To illustrate, tertiary amines include trialkylamines (such as triethylamine, tributylamine, diethylmethylamine, etc.), and heterocyclic compounds with five to nine total atoms in the ring structure including optionally substituted bi- and tricyclic heterocycles.

Ionic liquids are salts that are liquid at a temperature of 100° C. or below. Therefore, an ionic liquid comprises a cation moiety and an anion moiety. Throughout the present disclosure, a moiety of the formula [RQ]$^+$ (regardless of a superscript on R and/or Q) represents the cation moiety portion of the ionic liquid, and a moiety $R_F^-$ represents the anionic moiety portion of the ionic liquid.

The process of the invention typically includes reacting a compound of the formula Q with a quaternizing agent of the formula R$^1$X in the absence of a volatile solvent under conditions sufficient to produce a quaternary salt of the formula [R$^1$Q]$^+$X$^-$, where R$^1$ and Q are those defined herein and X is a leaving group. The term "quaternizing agent" refers to a compound of the general formula RX (regardless of the superscript on R and/or X) that when reacted with a compound Q that is a tertiary and having at least one lone pair of electrons forms a bond with Q to produce a quaternary cation moiety [RQ]$^+$, e.g., Q contains a total of four bonds. The term "leaving group" has the meaning conventionally associated with it in synthetic organic chemistry, i.e., an atom or a group capable of being displaced by a nucleophile and includes halo, acetoxy, mesyloxy, tosyloxy, trifluoromethanesulfonyloxy, 2,4-dinitrophenoxy, methoxy, N,O-dimethylhydroxylamino, as well as other leaving groups known to one skilled in the art of organic chemistry. The terms "halo" and "halide" are used interchangeable herein and refer to fluoro, chloro, bromo, or iodo. The phrase "in the absence of a volatile solvent" refers to having 25% by weight or less, typically 10% by weight or less, often 5% by weight or less, and most often no noticeable detection of a volatile solvent using a conventional analytical device. When describing a chemical reaction, the terms "treating," "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

A typical reaction condition for producing the quaternary salt of the formula [R$^1$Q]$^+$X$^-$ includes heating the reaction mixture to at least 20° C., typically at least 50° C., and often at least 100° C. The reaction mixture is generally heated for at least about 1 minutes, typically at least 30 minutes and often at least 48 hours. It should be appreciated that the scope of the invention is not limited to these particular reaction temperatures and times. Such reaction temperature and/or time can vary depending on the particular nature of reactants.

In some embodiments, the formation of the quaternary salt is carried out in a nonvolatile solvent. The use of a solvent can help avoid the precipitation of solid products or intermediates, and can help control the temperature rise in the case of exothermic reactions. The term "nonvolatile solvent" refers to a solvent having a pure component vapor pressure of 1 mm Hg or less, typically 0.1 mm Hg or less, and often 0.01 mm Hg or less at standard temperature. In one particular embodiment, a nonvolatile solvent is an ionic liquid. When a solvent is used, often the ionic liquid solvent is same compound as the ionic liquid being produced by the process of the invention. In this manner, a purification step can be eliminated. Moreover, the entire process can be conducted in a continuous manner. In fact, in some embodiments, at least a portion of the ionic liquid that is produced is used as the solvent for further reaction.

Because no volatile solvent is used, time and cost for purification or disposal of volatile solvent is eliminated. Accordingly, processes of the invention greatly reduce the overall cost and time for producing ionic liquids.

The process of the invention also includes reacting a quaternary salt of the formula [R$^1$Q]$^+$X$^-$ with an acidic (i.e., protonated) form of an ionic liquid counter anion compound of the formula HR$_F$ under conditions sufficient to produce said ionic liquid of the formula [R$^1$Q]$^+$R$_F^-$ and a volatile acid of the formula HX. The term "volatile acid" refers to an acidic compound having a pure component vapor pressure of 10 mm Hg or more, typically 760 mm Hg or more, and often 33,000 mm Hg or more at standard temperature. Alternatively, the term "volatile acid" refers to an acid that can be relatively readily removed from the reaction mixture under vacuum. Exemplary volatile acids include all haloacids (e.g., HF, HCl, HBr, and HI) as well as methanesulfonic acid, toluenesulfonic acid, carboxylic acids such as formic acid, acetic acid, etc., and other acids that at least 99% of which can be removed under vacuum (e.g., <10 mm Hg pressure) within 24 hours.

Generally, the reaction of quaternary salt with the acidic form of the ionic liquid counter anion compound is carried out at temperature of at least about −25° C., typically at least about 20° C. and often at least about 100° C. The reaction time between the quaternary salt and the acidic form of the ionic liquid counter anion compound is typically at least 1 hours, often at least 8 hours and sometimes at least 48 hours. However, the scope of the invention is not limited to these reaction temperatures and reaction times. In fact, the reaction temperature and/or reaction time can vary significantly depending on the nature of the quaternary salt and/or the ionic liquid counter anion compound.

The volatile acid that is produced in the reaction can be readily removed or separated from the desired ionic liquid. For example, since ionic liquids have a very low vapor pressure compared to the volatile acid, one can simply allow the volatile acid to evaporate from the reaction mixture or one can remove the volatile acid using a reduced pressure method.

The reaction of quaternary salt with the acidic form of the ionic liquid counter anion compound can also be carried out in a non-volatile solvent such as in an ionic liquid. When a solvent is used, often the ionic liquid solvent is same compound as the ionic liquid being produced by the process of the invention. In this manner, a purification step can be eliminated. Moreover, the entire process can be conducted in a continuous manner. In some embodiments, at least a portion of the ionic liquid that is produced by the process is used as the solvent for further reaction.

In one particular embodiment, the ionic liquid anion moiety is of the formula [YSO$_2$]$_2$N$^-$, wherein each Y is independently F or a fluorohydrocarbon. The term "fluorohydrocarbon" refers to a hydrocarbon moiety in which one or more hydrogen atoms are replaced with fluorine. In some embodiments, each Y is independently F or perfluorohydrocarbon. The term "perfluorohydrocarbon" refers to a hydrocarbon moiety in which all of the hydrogen atoms are replaced with fluorine.

In some embodiments, the ionic liquid anion is bis(trifluoromethylsulfonyl)imide ("TFSI") or bis(fluorosulfonyl)imide ("FSI").

One particular embodiment of a continuous process of the invention is illustrated in FIG. 1. As shown in FIG. 1, the step of producing a quaternization reaction to produce an intermediate cation salt is carried out in reactor 1. This reaction can be carried out in the presence of an ionic liquid as a solvent or without any added solvent. FIG. 1 illustrates that at least a portion of the ionic liquid that is produced in the process is used as the solvent. In reactor 2 of FIG. 1, the quaternary salt produced in reactor 1 is combined with an acid form of the desired anion to produce the ionic liquid.

Using the ionic liquid as a solvent prevents the intermediate cation salt from precipitating as a solid. The amount of ionic liquid solvent used in the reaction depends on the solubility of the intermediate quaternary salt that is produced. One of the advantages of the process illustrated in FIG. 1 is that since the solvent used in the reaction is the desired final product, there is no need to remove the solvent in later processing as would be required when using any other solvent.

The recycle stream may be heated or cooled in order to provide the desired temperature at the inlet to the quaternization process, i.e., reactor 1. Both the quaternization reactor (reactor 1) and the metathesis reactor (reactor 2) may be heated or cooled to maintain the reactant mixture in the desired temperature range. In some embodiments, the temperature range in reactor 1 is typically maintained between 20° C. and 200° C., often between 50° C. and 100° C. At lower temperatures, high recycle fractions (or a large amount of ionic liquid solvent) may be required to avoid precipitation of the intermediate cation salt, and at higher temperatures this intermediate salt may degrade. The reaction may be conducted in any reactor geometry known to those skilled in the art. In some embodiments, the reactor is equipped with heat exchange means to maintain the reactants in the desired temperature range. One advantageous geometry for the quaternization reactor (i.e., reactor 1) is a plug-flow reactor. In other embodiments, by adjusting the recycle rate and the recycle fluid inlet temperature, the reactor inlet and outlet temperatures can be maintained in the desired range without external heat exchange.

In one embodiment, the quaternizing agent is an alkyl halide which produces a halide salt of the desired cation intermediate. When an acid form of the desired anion is contacted with the quaternary salt, the metathesis byproduct is a volatile halide acid that can easily be removed.

Processes of the present invention have many advantages compared to conventional method for producing ionic liquids. For example, in some embodiments of the present invention no volatile solvents are used and no solid intermediate is produced. In addition, processes of the invention can easily be adapted for continuous production. Furthermore, processes of the invention do not require any water.

In some embodiments of the invention, the crude ionic liquid is further processed using a separation step where volatile reaction products are removed. This separation step can be any separation process known to those skilled in the art. One particular process is to use a stripping column wherein the crude ionic liquid is contacted with an inert gas and volatile reaction products are transferred to the inert gas stream. In an alternate embodiment, volatiles are removed by subjecting the crude ionic liquid to low pressure. Since the ionic liquid has low vapor pressure, any volatile impurities are easily removed.

The process of the invention is amenable to either in batch or continuous mode. In continuous process, a fraction of the produced ionic liquid can be recycled and used as the reaction solvent.

The ionic liquid produced by processes of the invention has a significantly lower water and/or impurity (e.g., halide) content than those produced using a conventional process. In some embodiments, ionic liquid produced by processes of the invention has water content of 1000 parts per million (ppm) or less, generally 100 ppm or less, typically 20 ppm or less and often 3 ppm or less. In other embodiments, the amount of impurity, e.g., halide, content in ionic liquids produced by processes of the invention is about 1000 ppm or less, generally 100 ppm or less, typically about 10 ppm or less, and often 1 ppm or less.

Scheme I below shows a typical prior art synthesis of the ionic liquid 1-propyl-1-butyl-pyrrolidinium bis(fluorosulfonyl)imide, or $PYR_{13}FSI$ (subscripts 1 and 3 represents methyl and propyl groups attached to pyrrolidine). In this synthesis, 1-methylpyrrolidine is mixed with 1-bromopropane to produce 1-propyl-1-butyl-pyrrolidinium bromide ($PYR_{13}Br$). This reaction is typically conducted in an organic solvent, and the solid $PYR_{13}Br$ precipitates from the solvent. The $PYR_{13}Br$ salt is then separated, dried, and mixed with an aqueous solution of a salt containing the desired anion, in this case lithium bis(fluorosulfonyl)imide or LiFSI. Metathesis between the pyrrolidinium salt and the lithium salt yields the desired ionic liquid $PYR_{13}FSI$. The product of the metathesis is a biphasic mixture with an organic ionic liquid ("IL") phase and an aqueous phase containing LiBr. If desired, extraction of the IL phase with water can be performed to remove any residual LiBr. The IL phase can contain several percent water, which must be removed by drying.

Scheme I. Prior Art Synthesis of $PYR_{13}FSI$

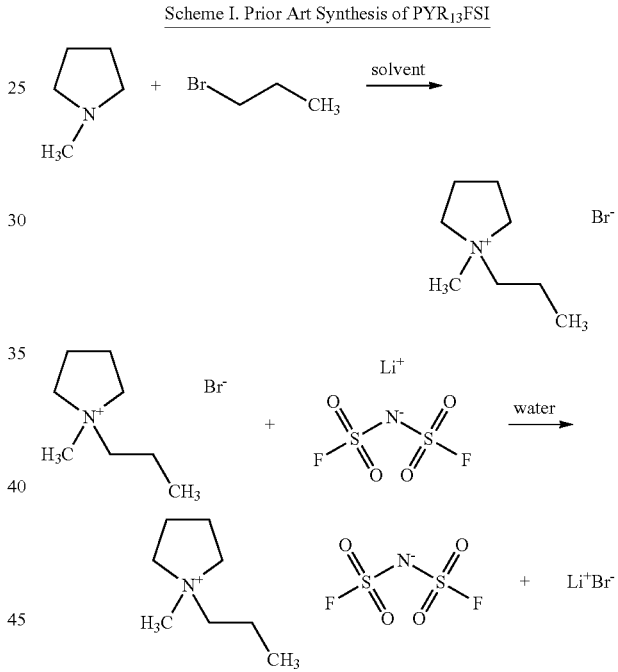

The process of Scheme I has several disadvantages for industrial production of ionic liquids. For example, the use of organic solvents in the quaternization step requires an energy-intensive step to remove the solvent and creates a waste stream and volatile organic compound ("VOC") emissions source. In addition, the presence of water in the second step of Scheme I necessitates drying of the ionic liquid that is produced. This drying step is especially important in electrochemical applications, which typically require water content in the ionic liquid to be at or below 100 ppm.

Scheme II below illustrates the production of a room-temperature ionic liquid, $PYR_{14}FSI$, according to one particular embodiment of the present invention. In contrast to the prior art method illustrated in Scheme I, the anion exchange is conducted with an acid (e.g., HFSI), rather than a salt (e.g., LiFSI), and the entire reaction is conducted using the product ionic liquid ($PYR_{14}FSI$) as a solvent.

Scheme 2. Synthesis of PYR$_{14}$FSI ionic liquid using one particular embodiment of the invention.

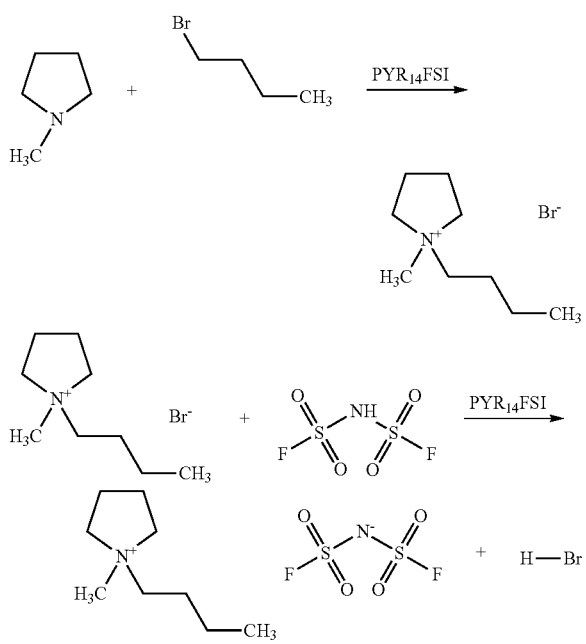

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Synthesis of PYR$_{14}$Br

In a three neck round bottom flask, equipped with a stirring bar, an addition funnel and an argon inlet, was placed N-methyl-N-butylpyrrolidinium bis(fluorosulfonyl)imide (50.5 g, 0.156 mole) at room temperature. To this mixture was added N-methylpyrrolidine (5.15 g, 0.0605 mole). 1-Bromobutane (8.29 g, 0.0605 mole) was placed in the addition funnel. The flask was heated with oil bath to reach the solution temperature to 75° C. 1-Bromobutane was added slowly dropwise over 5 minutes. The mixture was then heated to 85° C. for 2 h and 38 minutes and then cooled to room temperature and was evacuated for 30 minutes at 200 mTorr. Yield of N-methyl-N-butylpyrrolidinium bromide was 13.16 g (98%).

Example 2

Isolation of PYR$_{14}$Br Using Water

From Example 1 above, 6.10 g of homogeneous liquid (mixture of PYR$_{14}$Br and PYR$_{14}$FSI) at 85° C. was taken into a separatory funnel and cooled to room temperature. It was mixed with 6.10 mL of deionized water. The resulting mixture was allowed to separate for 30 minutes. The two phases were separated out in two different flasks. The lower phase was PYR$_{14}$FSI while aqueous upper phase contained PYR$_{14}$Br. Water was removed in vacuum to yield 1.15 g of PYR$_{14}$Br as a white solid (Yield 92.5%). The yield of separated PYR$_{14}$FSI was 4.56 g, (95%).

Example 3

Synthesis of PYR$_{14}$FSI without Water

From Example 1 above, 3.09 g (2.78 mmol PYR$_{14}$Br) of homogeneous liquid (mixture of 20% PYR$_{14}$Br and 80% PYR$_{14}$FSI) at 85° C. was placed in a 25 mL round bottomed flask with a magnetic stirrer and an argon inlet adaptor and was cooled to room temperature. Bis(fluorosulfonyl)imide (500 mg, 2.76 mmol) was added slowly without dilution in water. The resulting mixture was stirred at room temperature for 20 minutes. HBr that is produced in the reaction was removed at reduced pressure to yield 0.88 g (2.73 mmol) of additional PYR$_{14}$FSI. Thus, a total 3.32 g of PYR$_{14}$FSI was obtained, 2.47 g from the original solution and 0.88 g from the reaction.

Example 4

Synthesis of PYR$_{14}$FSI in Water

From Example 1 above, 40 g of homogeneous liquid (mixture of PYR$_{14}$Br and PYR$_{14}$FSI, 0.036 mol PYR$_{14}$Br) at 85° C. was placed in a 25 mL round bottomed flask with a magnetic stirrer and cooled to room temperature. It was mixed with 40 g of water followed by the addition of bis(fluorosulfonyl)imide (6.85 g, 0.037 mol). The resulting solution was mixed well in a separatory funnel and allowed to separate for 30 minutes. Ionic liquid was separated and washed with another 30 mL of water to give 43.31 g of PYR$_{14}$FSI (32 g from the initial solution and 11.31 g from the reaction).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for producing an ionic liquid of the formula [R$^1$Q]$^+$R$_F^-$, said process comprising:

reacting a compound of the formula Q with a quaternizing agent of the formula R$^1$X in the absence of a volatile solvent under conditions sufficient to produce a quaternary salt of the formula:

[R$^1$Q]$^+$X$^-$ reacting said quaternary salt with an acidic form of an ionic liquid counter anion compound of the formula HR$_F$ under conditions sufficient to produce said ionic liquid of the formula [R$^1$Q]$^+$R$_F^-$ and a volatile acid of the formula HX, wherein Q is an amine, phosphine, or arsine;

R¹ is a quaternizing moiety, such that [R¹Q]⁺ forms an ionic liquid cation;

X is a leaving group;

$R_F$ is an ionic liquid anion moiety.

2. The process of claim 1, wherein Q is an amine heterocycle moiety having three to six carbon atoms in the ring system.

3. The process of claim 2, wherein Q is selected from the group consisting of pyrrolidine, imidazole, pyridine, and piperidine, each of which is optionally substituted.

4. The process of claim 1, wherein Q is a tertiary amine, phosphine or arsine.

5. The process of claim 1, wherein no solid is produced during said process of producing said ionic liquid.

6. The process of claim 1, wherein the reaction temperature of said step of reacting said compound of formula Q with said quaternizing agent of the formula R¹X is in the range from about 50° C. to about 200° C.

7. The process of claim 1 further comprising the step of separating said volatile acid from said ionic liquid.

8. The process of claim 1, wherein said process for producing said ionic liquid is a continuous process.

9. The process of claim 1, wherein said ionic liquid anion moiety is of the formula $[YSO_2]_2N^-$, wherein each Y is independently F or a fluorohydrocarbon.

10. The process of claim 9, wherein each of Y is independently F or perfluorohydrocarbon.

11. The process of claim 10, wherein each of Y is independently F or trifluoromethyl.

12. The process of claim 9, wherein said ionic liquid anion is bis(trifluoromethylsulfonyl)imide or bis(fluorosulfonyl)imide.

13. The process of claim 1, wherein said step of reacting said compound of formula Q with said quaternizing agent of the formula R¹X is conducted in a nonvolatile solvent.

14. The process of claim 13, wherein said nonvolatile solvent is an ionic liquid solvent.

15. The process of claim 14, wherein said ionic liquid solvent is of the formula $[R^1Q]^+R_F^-$, wherein R¹, Q and $R_F$ are those defined in claim 1.

16. The process of claim 14, wherein at least a portion of said ionic liquid solvent is recycled.

17. The process of claim 14, wherein at least a portion of said ionic liquid that is produced is used as the ionic liquid solvent in said process.

18. The process of claim 1, wherein said volatile acid is removed by contacting said ionic liquid with an inert gas stream.

19. The process of claim 1, wherein said volatile acid is removed by subjecting the ionic liquid to a reduced pressure.

20. A process for producing an ionic liquid of the formula $[R^1Q^1]^+R^1_F^-$, said process comprising:

reacting a compound of the formula Q¹ with a quaternizing agent of the formula R¹X in the absence of a volatile solvent under conditions sufficient to produce a quaternary salt of the formula:

reacting said quaternary salt with a fluorinated acidic form of an ionic liquid counter anion compound of the formula $HR^1_F$ under conditions sufficient to produce said ionic liquid of the formula $[R^1Q]^+R^1_F^-$ and a volatile acid of the formula HX, wherein Q¹ is a tertiary amine, phosphine or arsine compound;

R¹ is a quaternizing moiety, such that [R¹Q¹]⁺ forms a quaternary ionic liquid cation;

X is a leaving group;

$R^1_F$ is a fluorinated ionic liquid anion moiety.

21. The process of claim 20, wherein Q¹ is a tertiary amine compound comprising a nitrogen-containing heterocycle with three to six carbon atoms in the ring system.

22. The process of claim 21, wherein said nitrogen-atom containing heterocycle compound is selected from the group consisting of pyrrolidine, imidazole, pyridine, and piperidine, each of which is optionally substituted.

23. The process of claim 20, wherein said ionic liquid anion moiety is of the formula $[YSO_2]_2N^-$, wherein each Y is independently F or a fluorohydrocarbon.

24. The process of claim 23, wherein each of Y is independently F or perfluorohydrocarbon.

25. The process of claim 24, wherein each of Y is independently F or trifluoromethyl.

26. The process of claim 23, wherein said ionic liquid anion is bis(trifluoromethylsulfonyl)imide or bis(fluorosulfonyl)imide.

* * * * *